US007260173B2

(12) United States Patent
Wakayama et al.

(10) Patent No.: US 7,260,173 B2
(45) Date of Patent: Aug. 21, 2007

(54) APPARATUS AND METHOD FOR DETECTING THREATS

(75) Inventors: Kyoichiro Wakayama, Yokohama (JP); Hiroya Koshishiba, Chigasaki (JP); Hidehiro Okada, Tokyo (JP); Yukiya Hattori, Hitachi (JP)

(73) Assignees: Hitachi, Ltd., Tokyo (JP); Hitachi Engineering & Services Co., Ltd., Ibaraki (JP)

( * ) Notice: Subject to any disclaimer, the term of this patent is extended or adjusted under 35 U.S.C. 154(b) by 0 days.

(21) Appl. No.: 10/372,393

(22) Filed: Feb. 25, 2003

(65) Prior Publication Data

US 2004/0101097 A1 May 27, 2004

(30) Foreign Application Priority Data

Nov. 25, 2002 (JP) ............................ 2002-340274

(51) Int. Cl.
*G01N 23/083* (2006.01)

(52) U.S. Cl. .......................................... 378/19; 378/57

(58) Field of Classification Search ................. 378/57, 378/19

See application file for complete search history.

(56) References Cited

U.S. PATENT DOCUMENTS

| | | | | |
|---|---|---|---|---|
| 3,466,439 | A * | 9/1969 | Setala | 378/65 |
| 4,686,695 | A * | 8/1987 | Macovski | 378/146 |
| 5,182,764 | A | 1/1993 | Peschmann et al. | |
| 5,367,552 | A | 11/1994 | Peschmann | |
| 5,600,700 | A * | 2/1997 | Krug et al. | 378/57 |
| 5,712,889 | A * | 1/1998 | Lanzara et al. | 378/19 |
| 5,796,802 | A | 8/1998 | Gordon | |
| 5,901,198 | A * | 5/1999 | Crawford et al. | 378/57 |
| 6,018,562 | A * | 1/2000 | Willson | 378/9 |
| 6,236,709 | B1 * | 5/2001 | Perry et al. | 378/57 |
| 6,334,708 | B1 * | 1/2002 | Kosugi | 378/197 |
| 6,339,632 | B1 * | 1/2002 | Besson | 378/15 |
| 6,473,487 | B1 * | 10/2002 | Le | 378/57 |
| 2005/0169422 | A1 * | 8/2005 | Ellenbogen | 378/57 |

FOREIGN PATENT DOCUMENTS

| | | |
|---|---|---|
| JP | 8327525 | 12/1996 |
| JP | 1090202 | 4/1998 |
| JP | 11500229 | 1/1999 |
| JP | A-2001-235434 | 8/2001 |

* cited by examiner

*Primary Examiner*—Edward J. Glick
*Assistant Examiner*—Thomas R. Artman
(74) *Attorney, Agent, or Firm*—Mattingly, Stanger, Malur & Brundidge, P.C.

(57) ABSTRACT

An image pickup unit is disposed so as to be able to obtain a scan projection image of an inspection subject from each of a vertical direction and a horizontal direction. An X-ray absorption coefficient of an object in the inspection subject is obtained from the vertical scan projection image and the horizontal scan projection image. It is determined whether there is a threat in the inspection subject on the basis of the X-ray absorption coefficient. Furthermore, a CT image is obtained by moving the image pickup unit around the inspection subject. It is determined whether there is a threat in the inspection subject, on the basis of the CT values of the CT image.

2 Claims, 6 Drawing Sheets

| SHAPE | (1) CUBOID | (2) BALL | (3) CYLINDER | (4) CYLINDER | (5) CUMULATED CUBOIDS |
|---|---|---|---|---|---|
| VERTICAL IMAGE | | | | | |
| HORIZONTAL IMAGE | | | | | |

APPARATUS AND METHOD FOR DETECTING THREATS

BACKGROUND OF THE INVENTION

The present invention relates to a threat detection apparatus and a threat detection method, and in particular to a threat detection apparatus and a threat detection method using X-rays.

As for reference relating to the present invention, a threat detection apparatus that radiates X rays having two energy levels alternately is described in JP-A-2001-235434. A threat detection apparatus using a combination of scan projection and CT (Computed Tomography) is described in U.S. Pat. No. 5,182,764. In addition, a threat detection apparatus using a combination of scan projection and X-ray tubes (two tubes) differing in energy is described in U.S. Pat. No. 5,367,552.

These threat detection apparatus utilize large-sized X-ray CTs of high speed. The threat detection apparatus can also detect explosives that are hard to detect in inspection apparatus using X-ray transmission seen in airports in Japan, and they are used mainly in large-sized airports in United States. However, these apparatus are as heavy as 3 tons to 7 tons, and hard to move. Therefore, the degree of freedom in layout cannot be obtained. The reasons why these apparatus become large in size and mass are as follows: (1) Since a CT image is obtained with continuous rotation, the structure of slip rings becomes complicated. (2) A high output X-ray tube and a high voltage power supply (HVPS) are needed so that an X-ray is not absorbed by a conveyor belt even if the X-ray is incident on the conveyor belt at a shallow angle in order to pick up a CT image on the conveyor belt.

For small-sized airports such as Narita and Haneda, a threat detection apparatus that is small in apparatus size, small in mass, low in price, and high in precision is needed. For that purpose, it is necessary to solve the problems of (1) and (2).

Since threat detection apparatus are operated every day, a threat detection apparatus that is long in life and small in the number of times of maintenance is also needed.

SUMMARY OF THE INVENTION

According to the present invention, a threat detection apparatus that is small in size, light in mass, movable, good in maintainability, low in price, and capable of detecting a threat incorporated in an inspection subject, is provided.

A threat detection method for detecting a threat incorporated in an inspection subject efficiently is also provided.

An image pickup unit is disposed so as to be able to obtain a scan projection image of an inspection subject from each of a vertical direction and a horizontal direction. An X-ray absorption coefficient of an object in the inspection subject is obtained from the vertical scan projection image and the horizontal scan projection image. It is determined whether there is a threat in the inspection subject on the basis of the X-ray absorption coefficient.

Furthermore, a CT image is obtained by moving the image pickup unit around the inspection subject. It is determined whether there is a threat in the inspection subject, on the basis of CT values of the CT image.

By providing two belt conveyors for moving an inspection subject and preventing the belt conveyors from intercepting an X-ray path of an X-ray generator and an X-ray detector, inspection is conducted with a low X-ray output. In addition, by forming a CT scanner using a swing type and eliminating a sliding portion (slip ring), maintenance is simplified.

Other objects, features and advantages of the invention will become apparent from the following description of the embodiments of the invention taken in conjunction with the accompanying drawings.

BRIEF DESCRIPTION OF THE DRAWINGS

Preferred embodiments of the present invention will now be described in conjunction with the accompanying drawings, in which.

DESCRIPTION OF THE EMBODIMENTS

Hereafter, embodiments of the present invention will be described with reference to the drawings.

Figure 1:
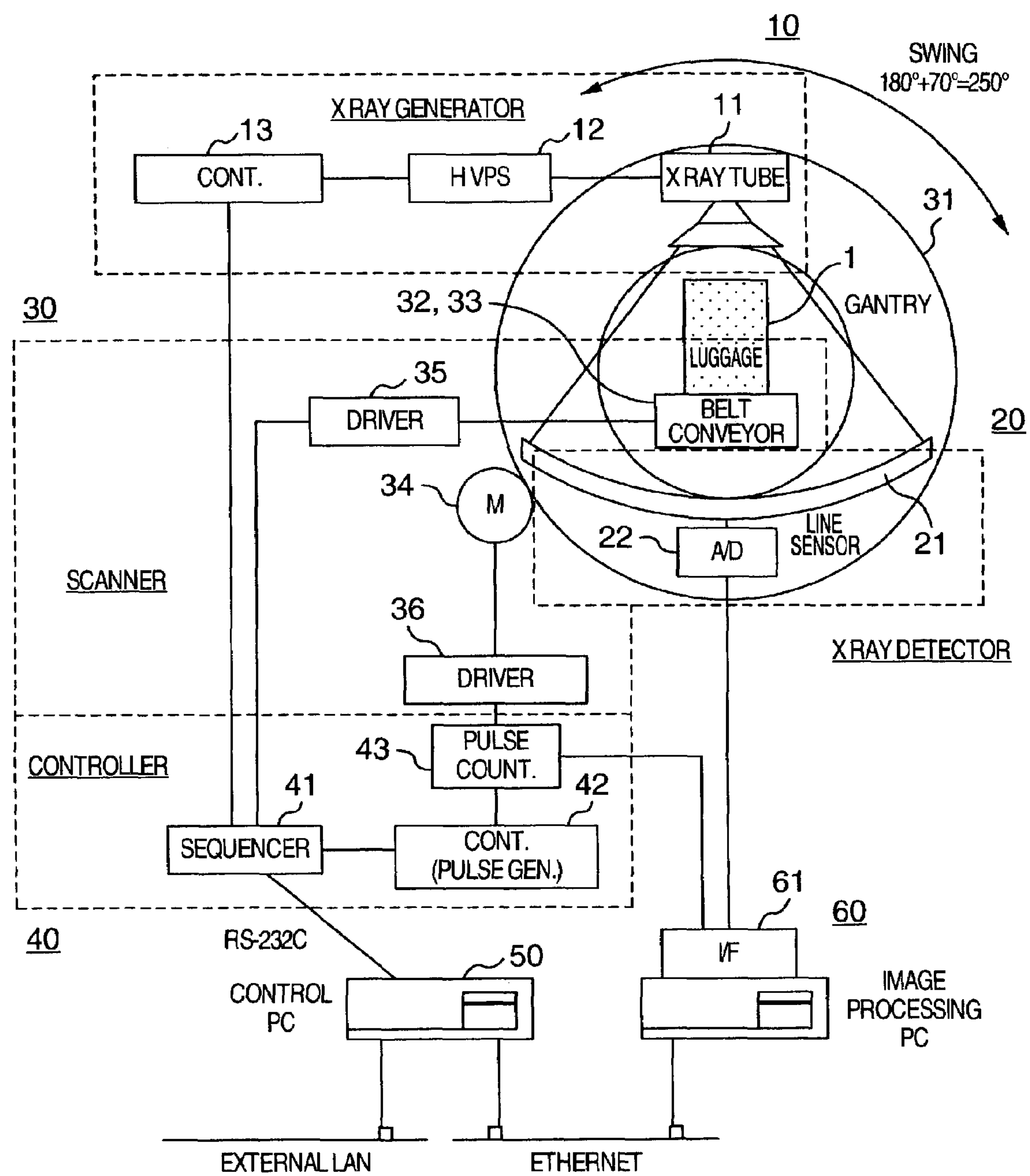
FIG. 1 is a block diagram of a threat detection apparatus in an embodiment of the present invention.
Figures 2, 5:
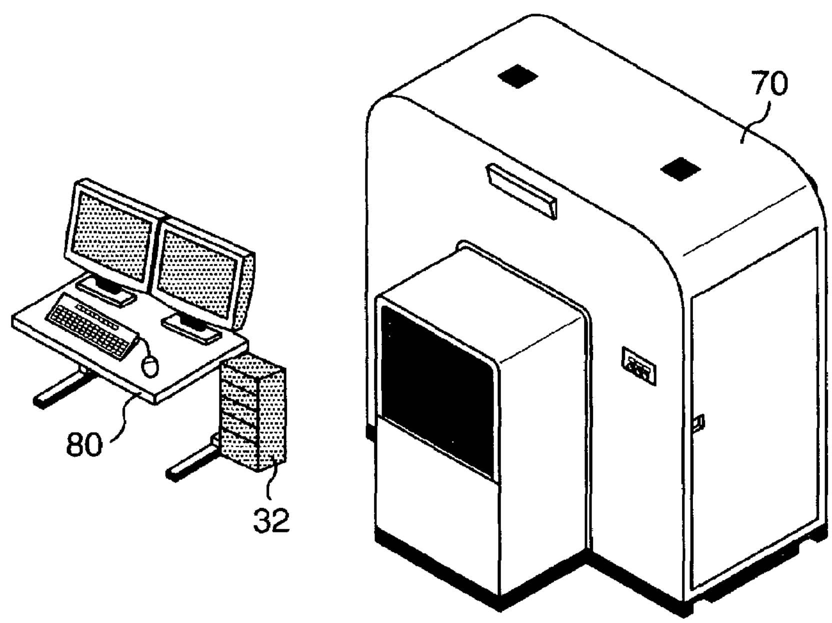
FIG. 2 is an oblique exterior view of a threat detection apparatus in an embodiment of the present invention.
FIG. 5 is a diagram showing shapes judged on the basis of scan projection images obtained by changing the direction, in an embodiment of the present invention.
Figure 3:
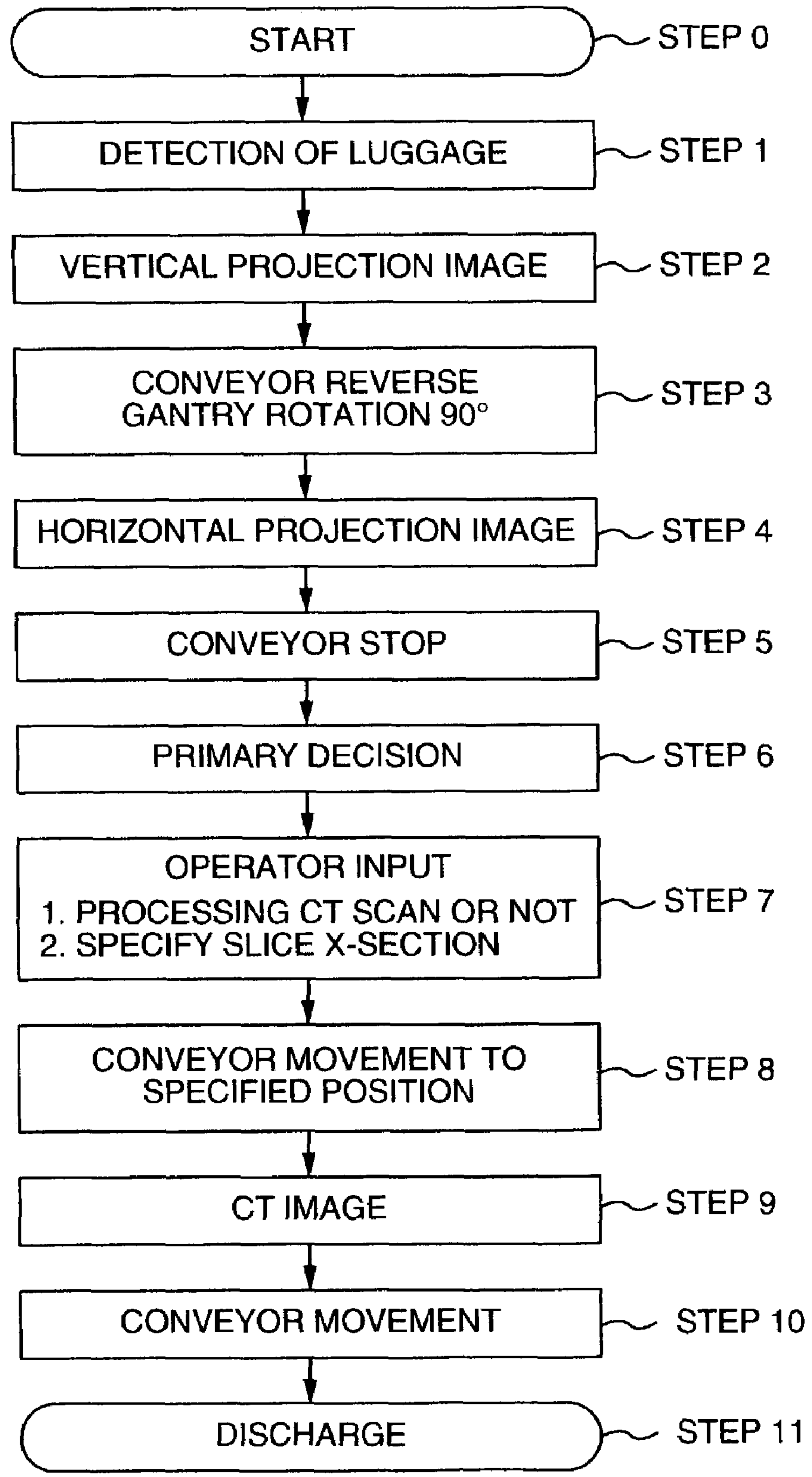
FIG. 3 is a diagram showing an operation flow a threat detection apparatus in an embodiment of the present invention.
Figure 4A:
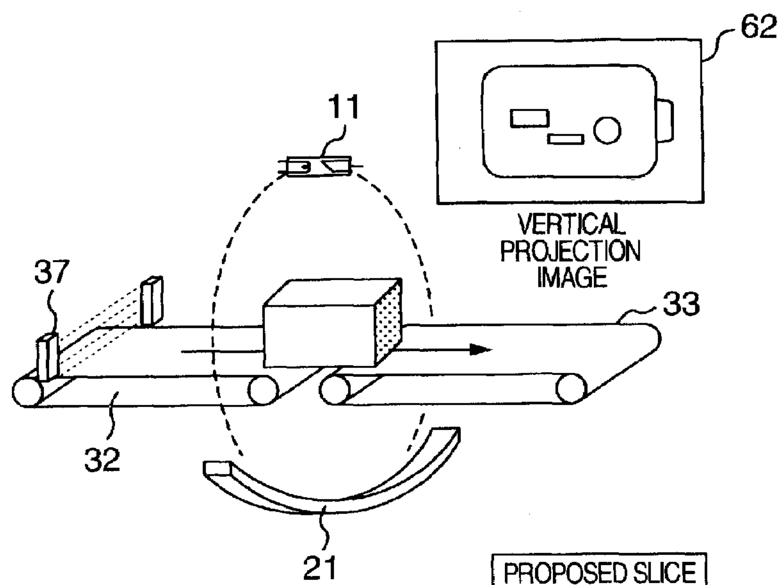
FIGS. 4A to 4C are oblique views and screen display diagrams showing operation of a threat detection apparatus in an embodiment of the present invention.
Figure 4B:
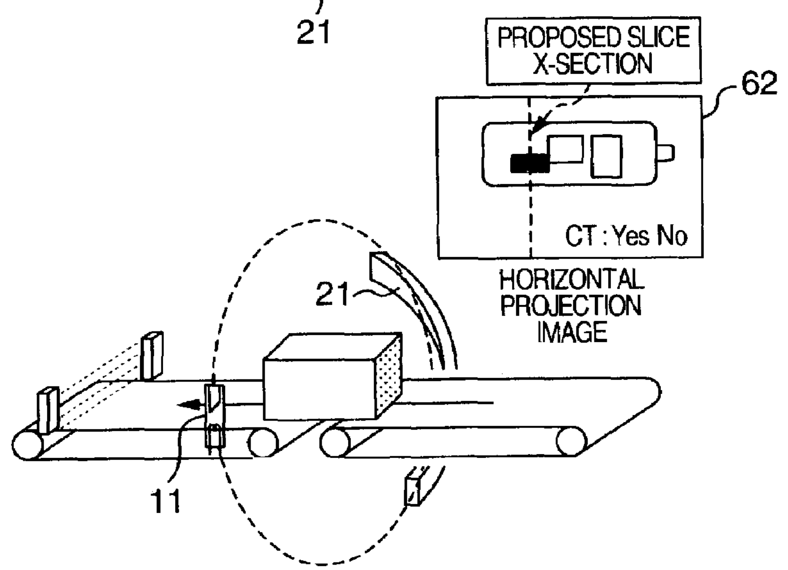
Figure 4C:
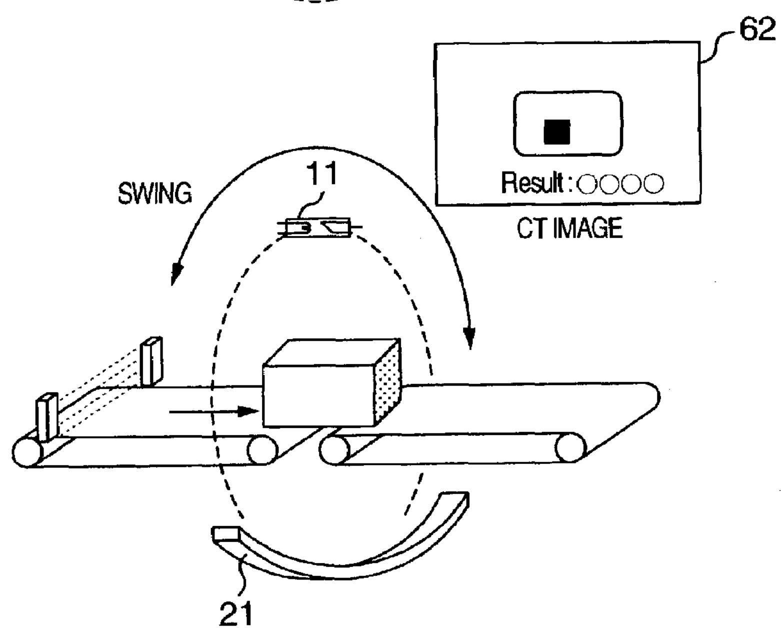
Figure 6:
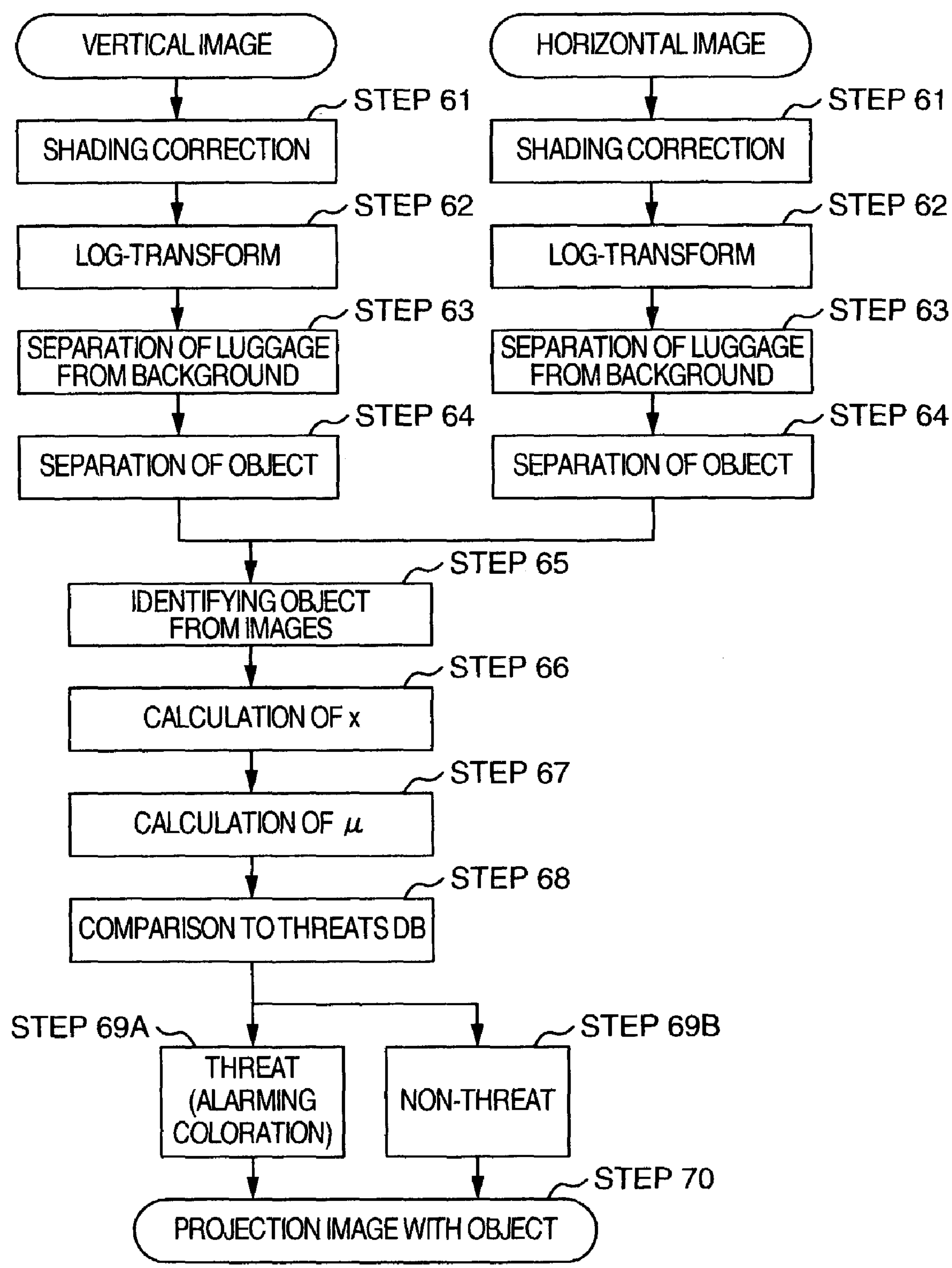
FIG. 6 is a flow diagram showing a procedure for determining whether a threat is included in luggage on the basis of a scan projection image, in an embodiment of the present invention.
Figure 7:
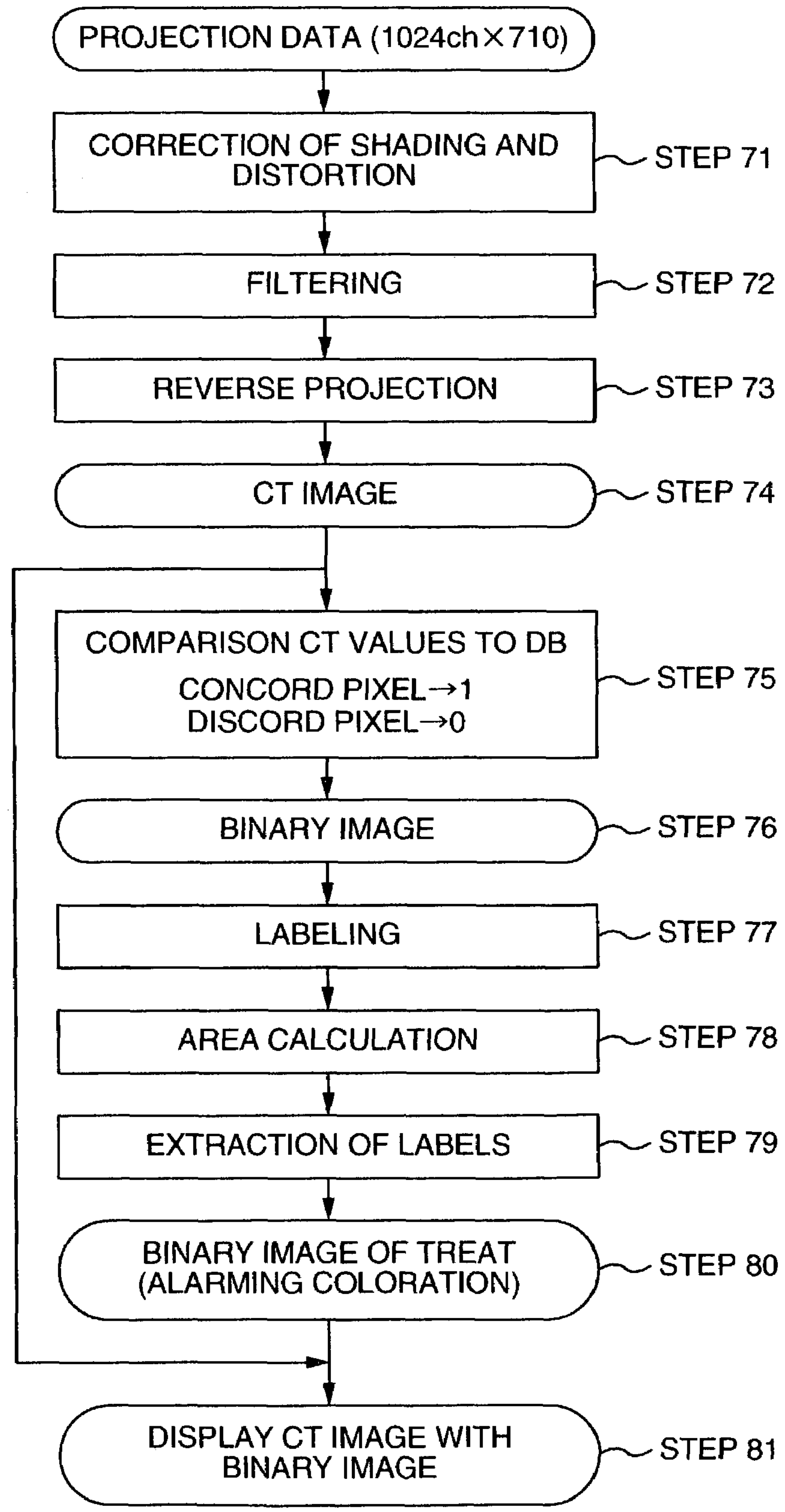
FIG. 7 is a flow diagram showing a procedure for determining whether a threat is included in luggage on the basis of CT values, in an embodiment of the present invention.

First, an embodiment of a threat detection apparatus according to the present invention will now be described with reference to FIGS. 1 to 7. FIG. 1 is a block diagram of a threat detection apparatus. FIG. 2 is an oblique exterior view of a threat detection apparatus. FIG. 3 is a diagram showing an operation flow a threat detection apparatus in an embodiment of the present invention. FIGS. 4A to 4C are oblique views and screen display diagrams showing operation of a threat detection apparatus. FIG. 5 is a diagram showing shapes judged on the basis of scan projection images obtained by changing the direction. FIG. 6 is a flow diagram showing a procedure for determining whether a threat is included in luggage on the basis of a scan projection image. FIG. 7 is a flow diagram showing a procedure for determining whether a threat is included in luggage on the basis of CT values.

Herein, the threats include but to limited to flammable materials, combustion-sustaining materials, combustible materials, explosives, fireworks, matches, guns and knives.

As shown in FIG. 1, the threat detection apparatus 100 in this embodiment includes an X-ray generator 10, an X-ray detector 20, a scanner 30, a controller 40, a control PC (personal computer) 50, and an image processing PC 60. The X-ray generator 10 includes an X-ray tube 11 having a radiation angle of 70 degrees and a rating of 3 mA at 160 kV disposed on a gantry 31 described later, its high voltage power supply 12, and an X-ray controller 13. The X-ray detector 20 includes a line sensor 21, which includes a plurality of scintillators and a plurality of photodiode arrays disposed so as to be opposed to the X-ray tube 11 on the gantry 31, and an A/D converter 22. The X-ray tube 11 and the line sensor 21 form an image pickup device. By using this image pickup device, an X-ray transmission image and a CT sectional image of an inspection object can be obtained.

The scanner 30 includes the gantry 31, which takes the shape of a hollow disc and which can rotate around luggage 1 to be inspected, by at least 330 degrees, belt conveyors 32 and 33 for conveying the luggage 1, a servomotor 34 for rotating the gantry 31 around an axis perpendicular to paper, and motor drivers 35 and 36. The controller 40 is controlled by the control PC 50. The controller 40 includes a sequencer 41 for controlling the X-ray controller 13, the driver 35 and a controller 42, the controller 42 for generating control pulses to control the rotation of the servomotor 34 in accordance with an order from the sequencer 41, and a pulse counter 43 for sending a pulse to the image processing PC 60. An I/F board 61 is inserted in the image processing PC 60. The image processing PC 60 takes in an X-ray image signal output from the A/D converter 22 and conducts processing thereon. The image processing PC 60 is connected to the control PC 50 via Ethernet, and communication is conducted between the PCs.

FIG. 2 shows an exterior view of the threat detection apparatus 100. A main body includes a chassis 70, an inlet side belt conveyor 32, and an outlet side belt conveyor 33, which is not illustrated. The control PC, two displays for displaying a projection image and a CT image, a keyboard, and a mouse are disposed on an operator console 80.

Referring back to FIG. 1, operation of the threat detection apparatus 100 will now be described. When a high voltage is applied to the X-ray tube 11 under the control of the X-ray controller 13, the X-ray is radiated in a fan form with a radiation angle of 70 degrees. The scintillators in the line sensor 21 attached to the gantry 31 in a circular arc form so as to be opposed to the X-ray tube 11 receive the X-ray and emit light. The light is subjected to O/E conversion by the photodiode arrays disposed behind the scintillators. As for the scintillators, sixteen scintillators each having a width of 1.6 mm and a length of 102.4 mm are disposed in a circular arc form. As for the photodiode arrays, sixteen photodiode arrays each having a pitch of 1.6 mm and 64 channels are used in the same way as the scintillators. The line sensor has an overall length of 1.64 m and 1,024 channels.

If the intensity of the X-ray that has arrived at scintillator is high, then the scintillator emits intense light, and electric signal resulting from conversion conducted in photodiodes also becomes intense. When metal is in the luggage, the X-ray is absorbed by metal and the electric signal also becomes weak. Since each threat has a peculiar X-ray absorption coefficient, it is necessary to conduct A/D conversion on its electric signal with high precision. In the present embodiment, an analog signal from the line sensor 21 is converted to a digital signal by the A/D converter 22 having a resolution of 16 bits, and the digital signal is transferred to the image processing PC 60.

Since the signal supplied from the line sensor 21 is a one-dimensional signal, the image processing PC 60 creates a two-dimensional transmitted X-ray intensity image in conformity with movement of the luggage 1 moved by the belt conveyors 32 and 33, and displays the transmitted X-ray intensity image on a display monitor via the control PC. Guns and knives can be identified on this monitor picture and a monitor picture from a perpendicular position described later.

On the other hand, an X-ray CT sectional image of the luggage 1 and its contents is obtained by stopping the movement of the luggage 1, swinging the gantry 31 having the image pickup device mounted thereon, and detecting a signal while rotating the gantry 31 by 250 degrees. The 250 degrees is the sum of 180 degrees, which provides a sectional image in a CT apparatus that generates the X-ray in a fan form, and the X-ray radiation angle 70 degrees. Unlike the conventional threat detection apparatus, the threat detection apparatus 100 in the present embodiment does not conduct continuous rotation, but conducts half rotation operation. Therefore, the complicated slip ring mechanism for supplying the high voltage to the X-ray tube and taking out the signal from the line sensor is not necessary, and consequently the size and the price can be reduced. In addition, since there are no sliding portions, the life is long and the number of times of maintenance can be reduced. Since movement motion on the circular arc in one direction is conducted, sections for acceleration and deceleration (40 degrees×2) are required before and after the signal detection section (250 degrees), and a rotation angle of the gantry equivalent to at least 330 degrees is required. The detection time includes 0.5 seconds for acceleration, 2 seconds for the signal detection time, and 0.5 seconds for deceleration.

Detection operation of the threat detection apparatus 100 will now be described with reference to FIGS. 3 and 4. With reference to FIG. 3, an optical sensor 37 disposed at an inlet of the inlet side belt conveyor 32 detects that luggage has entered the apparatus (step 1). This causes regular rotation of the belt conveyors 32 and 33, and causes the luggage 1 to pass through an X-ray radiation unit, which is not illustrated. In addition, an X-ray radiation is started. As a result, the image processing PC 60 creates a scan projection image in the vertical direction, and it is displayed on a monitor 62 (step 2). FIG. 4A shows a principal part of the threat detection apparatus 100 at this time. The gantry is fixed in an original position, in which an X-ray beam is radiated vertically downward. A vertical scan projection image shown on the monitor 62 is displayed after the luggage 1 has passed through an X-ray scan projection unit.

Subsequently, the gantry 31 is rotated by 90 degrees clockwise when seen from the inlet side, and the belt conveyors 32 and 33 are reversed (step 3). The luggage 1 is passed through the X-ray radiation unit, which is not illustrated. As a result, a horizontal projection image is taken in by the image processing PC 60 (step 4). After the belt conveyors 32 and 33 have been stopped (step 5), the horizontal scan projection image and a primary decision result are displayed on the monitor 62 (step 6). FIG. 4B shows a principal part of the threat detection apparatus 100 at this time. The gantry having the image pickup device mounted thereon is fixed in a position rotated clockwise by 90 degrees. In this position, the X-ray beam transmits through the luggage 1 from the lateral direction (horizontal direction). After the luggage 1 has passed through the X-ray scan projection unit, the horizontal scan projection image shown on the monitor 62 is displayed. The present apparatus displays a container having an X-ray absorption coefficient judged to be a threat in the primary decision on the basis of the vertical and horizontal scan projection images, with, for example, a red color on the picture. With this picture, an input as to whether a slice image detection using CT is necessary and an input of a slice Cross section to be detected are waited for. In order to accept an input which specifies the slice Cross section on the picture, a cursor for inputting the CT slice Cross section is also displayed (step 7).

The operator decides to display a CT sectional image, selects a CT slice Cross section, and inputs them by using the keyboard and the mouse. The belt conveyors 32 and 33 are driven so as to obtain the selected CT slice Cross section, and the luggage 1 is fixed. For example, by counting control pulses for driving the belt conveyors 32 and 33 and resetting a counter at a start position of a scan projection image, the scan projection image can be aligned with the position of the actual luggage 1. The gantry moves to a swing origin for the CT (step 8). Subsequently, the present apparatus creates a CT image every time X-ray absorption data is acquired while rotating and moving the gantry. It is determined to whether a threat is included in the luggage 1 by comparing the CT image with a database separately held (secondary decision) and a result is displayed (step 9). With this picture displayed, the belt conveyors are moved in the regular direction (step 10). The luggage is discharged (step 11).

If it is judged at the step 6 that a threat is not included, then the processing proceeds to the step 10 as it is. The optical sensor 37 is shown in FIGS. 4A to 4C to be disposed only on the inlet side of the inlet belt conveyor 32. However, the optical sensor 37 may be disposed on the outlet side. The optical sensor 37 may be disposed on the inlet side and the outlet side of the outlet belt conveyor 33.

As for the scan projection images, the order in the first scan projection image in the vertical direction and second scan projection image in the horizontal direction may be reversed, i.e., the first scan projection image may be the scan projection image in the horizontal direction and the second scan projection image may be the scan projection image in the vertical direction. When the belt conveyors are inclined, any orthogonal directions may be selected. The directions need not be orthogonal.

Since two belt conveyors are used in the present embodiment, there is no belt conveyor in the X-ray path, and consequently the X-ray is not absorbed by the belt conveyor. Whether there is a conveyor belt does not pose a problem in X-ray transmission. If there is a belt conveyor, however, then the X-ray transmitted through the width (80 cm) direction of the belt at a shallow angle during the swing operation in the X-ray CT is absorbed by the belt extremely greatly. With an application voltage of approximately 160 kV, therefore, the X-ray is not transmitted in some cases. If data includes a point through which the X-ray is not transmitted, the sectional image cannot be reconstructed. In this case, therefore, it is necessary to raise the tube voltage to approximately 180 kV. If the tube voltage is raised, however, both the high voltage power supply and the X-ray tube become large-sized and the gantry having the X-ray tube mounted thereon also becomes large-sized.

Since in the present embodiment the belt is excluded from the X-ray path, the X-ray output can be reduced and a small-sized low-priced X-ray source can be used. Since the X-ray source is light in weight, the gantry rotation unit can also be made small in size and weight. In addition, there is no measurement error due to absorption by the conveyor belt, and an accurate CT image can be detected.

A method for presuming the shape of an object in the luggage on the basis of the image in the vertical direction and the image in the horizontal direction will now be described with reference to FIG. 5. With reference to FIG. 5, if both the vertical scan projection image and the horizontal scan projection image are quadrangles each having a uniform absorption coefficient, the shape of the object can be presumed to be a cuboid. In the same way, a ball can be judged from circles each having a nonuniform absorption coefficient. A cylinder can be judged from a quadrangle having a nonuniform absorption coefficient in one of the pictures and a circle having a uniform absorption coefficient in the other of the pictures, or from quadrangles each having a nonuniform absorption coefficient.

In the present embodiment, the vertical scan projection image and the horizontal scan projection image are obtained, and consequently the thickness of the substance can be obtained. It is possible to derive the absorption coefficient of the substance therefrom.

Denoting intensity of X-ray incident on the substance by $I_0$, thickness of the substance by x, and X-ray absorption coefficient of the substance by μ, intensity I of the transmitted X-ray is given by the following equation.

$$I=I_0\exp(-\mu\cdot x) \tag{1}$$

I can be obtained from the X-ray intensity of the object portion in the vertical scan projection image. $I_0$ can be obtained from the X-ray intensity of the background, and x can be obtained from the thickness of the object in the horizontal scan projection image. Therefore, μ can be calculated by the following equation, which is obtained by rewriting the equation (1).

$$\mu=\{In(I_0)-In(I)\}/x \tag{2}$$

Even in the case where two substances are cumulated as shown in (5) in FIG. 5, an overlying substance 2 and an underlying substance 3 might not be completely cumulated in the horizontal scan projection image. In this case, the X-ray absorption coefficient of the substance 2 can be obtained by setting $I_0$ in the equation (2) equal to an X-ray intensity (background) of a portion containing only the substance 3 and setting 1 equal to an X-ray intensity of a portion where the substance 2 and the substance 3 are cumulated. Even in the case where the substances are completely cumulated, it is a matter of course that the X-ray absorption coefficient can be obtained from the equation (2) by obtaining I and $I_0$ from the horizontal scan projection image and obtaining x from the vertical scan projection image.

The calculated X-ray absorption coefficient is compared with an X-ray absorption coefficient database of threats stored in the image processing PC, and subjected to primary decision.

The method for detecting a threat from the scan projection images will now be described in more detail with reference to FIG. 6. The vertical scan projection image obtained by the image processing PC shown in FIG. 1 is subjected to shading correction as to distortion of the projection system, unevenness in X-ray intensity, and sensitivity dispersion in the line sensor (step 61). Then the vertical scan projection image is subject to logarithmic transformation (step 62). The luggage is separated from the background (step 63). And separation of an object in the luggage is executed (step 64). In the horizontal scan projection image as well, similar processing is conducted. Thereafter, edge association is conducted and thereby object identification is executed between the vertical scan projection image and the horizontal scan projection image (step 65). A transmission length x of the object is obtained from one of the images (step 66). The X-ray absorption coefficient of the object portion and the X-ray absorption coefficient of the background are obtained from the other of the images, and the X-ray absorption coefficient is calculated (step 67). The obtained X-ray absorption coefficient is compared with the database of the X-ray absorption coefficients of threats (step 68). If the object is judged to be a threat on the basis of a predetermined criterion, then the position of the object is indicated by, for example, red (step 69A). The object is displayed so as to be superposed on either of the two scan projection images (step 70). If concord with the database is not obtained, then coloring is not especially conducted.

Calculation of the object dimension x and calculation of the X-ray absorption coefficient are executed by a computation unit in the image processing PC. However, the calculations may be executed by another PC.

In order to input a CT slice Cross section position, the operator selects a central portion of an object judged to be a threat, and displays the cross section (line) on the picture displayed at the step 70. The operator determines whether the CT image pickup can be executed. When executing the CT image pickup, the operator moves the cross section (line) to a desired position with the mouse, and determines a slice position.

In the decision using the X-ray absorption coefficient, a substance having an X-ray absorption coefficient similar to that of a threat is also screened. In the threat detection apparatus of the present embodiment, therefore, a sectional image of a pertinent place of luggage judged to include a threat in the primary decision is obtained in the X-ray CT. In this process, a scale called CT value is obtained. This CT value is given by the following equation.

$$CT\text{ value}=K(\mu-\mu_w)/\mu_w \quad (3)$$

In the equation (3), $\mu$ is a linear absorption coefficient of a voxel (a minimum unit volume of CT), K is a constant 1,000, and $\mu_w$ is a linear absorption coefficient of water. Since the linear absorption coefficient of air is 0, its CT value is −1,000. Water has a CT value of 0, and a bone has a value of 1,000. The CT value has such a wide scale. Therefore, the CT value is compared with the CT value database of threats stored in the image processing PC, and the CT value can be used in a secondary decision together with the sectional image using the CT.

The threat detection method using the X-ray CT will now be described in more detail with reference to FIG. 7. The threat detection apparatus of the present embodiment rotates around luggage at a constant speed over 250 degrees, which is the sum of 180 degrees and the X-ray radiation angle of 70 degrees, and detects a signal. The threat detection apparatus collects projection data of 710 points during rotation of 250 degrees, and executes correction of the shading and projection system distortion (step 71). As for projection data after correction, filtering computation (step 72) and back projection computation (step 73) are conducted, and a CT image, which is a reconstructed image, is displayed (step 74). Since the calculation quantity of the reconstruction computation of the CT image is enormous, an expensive DSP (Digital Signal Processor) board is typically used in many cases. In the present apparatus, however, dual-CPU PC is used to reduce the price.

The CT value of each pixel of the CT image is compared with the CT value database of the threats stored in the image processing PC. Pixels are classified into concord pixels and discord pixels on the basis of a predetermined permissible difference (step 75). As a result, a binary image can be obtained (step 76). After labeling processing (step 77) for dividing a binary image region, a pixel area for each of classified labels is counted (step 78). Labels each having an area greater than a predetermined area are extracted (step 79). The extracted labels are converted to, for example, red indication (step 80). The binary image is displayed so as to be superposed on the CT image obtained at the step 74 (step 81).

It is also possible to replace the object indicated with a red color at the step 80 by the object in luggage indicated at the step 64 in FIG. 6, and display the object on the vertical scan projection image or the horizontal scan projection image.

Although the filtering computation and the back projection computation are executed in the computation unit in the image processing PC, it is also possible to execute them in a different PC.

The tube voltage of the X-ray CT is 160 kV. At this time, X-ray energy is intense at approximately 100 keV. On the other hand, if the tube voltage is set equal to 80 kV, then the X-ray energy becomes intense at approximately 50 keV. A mass absorption coefficient for X-ray ($\mu/\rho$) depends on energy, and the CT value defined by the equation (3) also depends on energy. If the CT values obtained by two X-ray CTs respectively of 160 kV and 80 kV are compared with databases for respective voltages and an AND function is performed on threat decisions, then a threat detection apparatus having higher precision can be obtained.

In the embodiment, hardware control is conducted by a program written in a memory of the control PC. It can be controlled by hardware as well.

According to the present invention, a threat detection apparatus that is small in size, light in mass, movable, low in price, and capable of detecting a threat incorporated in an inspection subject is obtained. A threat detection apparatus that is excellent in maintainability and low in price is also obtained. In addition, a threat detection method for detecting a threat incorporated in an inspection subject efficiently is obtained.

It should be further understood by those skilled in the art that although the foregoing description has been made on embodiments of the invention, the invention is not limited thereto and various changes and modifications may be made without departing from the spirit of the invention and the scope of the appended claims.

We claim:

1. A hazardous material detection system comprising:

a gantry provided with an X-ray source and an X-ray sensor which are disposed in opposition to each other, wherein the X-ray source comprises a cable for supplying power and the X-ray sensor comprises a cable for outputting a signal and wherein the gantry swings forward and backward on a circular arc around an inspection subject but does not continuously rotate;

a belt-conveyor which conveys the inspection subject wherein the belt-conveyor comprises a first conveyor in front of the gantry and a second belt-conveyor in rear of the gantry;

a calculating unit which calculates a computed tomography (CT) value by swinging the gantry forward and backward along the circular arc around the inspection subject along said circular arc and picking up a CT image of the inspection subject; and a display unit which displays the X-ray absorption coefficient and the CT value, wherein the CT image is obtained by use of a particular configuration of the gantry which allows the gantry to rotate at least 330 degrees.

2. A method for detecting hazardous material, wherein a gantry is provided with an X-ray source and an X-ray sensor which are disposed in opposition to each other, the X-ray source comprises a cable for supplying power and the X-ray sensor comprises a cable for outputting a signal, and the gantry swings forward and backward on a circular arc around an inspection subject but does not continuously rotate, the method comprising the steps of:

conveying an inspection subject by moving a belt-conveyor comprising a first belt-conveyor in front of the gantry and a second belt-conveyor in rear of the gantry, and then stopping the belt-conveyor if the inspection subject is positioned between the first belt-conveyor and the second belt-conveyor;

swinging the gantry forward and backward along the circular arc while an X-ray is being radiated from the X-ray source;

obtaining a computed tomography (CT) image based on an X-ray radioscopy data obtained by the X-ray sensor, wherein the CT image is obtained by use of a particular configuration of the gantry which allows the gantry to rotate at least 330 degrees; and displaying the CT image on a display device.

* * * * *